United States Patent
De Haan et al.

(10) Patent No.: US 10,017,451 B2
(45) Date of Patent: *Jul. 10, 2018

(54) LACTIC ACID EXTRACTION (71) Applicant: PURAC BIOCHEM BV, Gorichem (NL)

(72) Inventors: André Banier De Haan, Best (NL); Jan Van Krieken, Gorinchem (NL); Tanja Đekic Živkovic, 's-Hertogenbosch (NL)

(73) Assignee: PURAC BIOCHEM B.V., Gorinchem (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/366,595

(22) PCT Filed: Dec. 21, 2012

(86) PCT No.: PCT/EP2012/076696
§ 371 (c)(1),
(2) Date: Jun. 18, 2014

(87) PCT Pub. No.: WO2013/093028
PCT Pub. Date: Jun. 27, 2013

(65) Prior Publication Data
US 2014/0335581 A1  Nov. 13, 2014

Related U.S. Application Data (60) Provisional application No. 61/579,730, filed on Dec. 23, 2011.

(30) Foreign Application Priority Data

Dec. 23, 2011 (EP) .................................. 11195691

(51) Int. Cl.
C07C 51/48 (2006.01)
C12P 7/56 (2006.01)
B01D 11/04 (2006.01)
C07C 51/41 (2006.01)

(52) U.S. Cl.
CPC ............... *C07C 51/48* (2013.01); *B01D 11/04* (2013.01); *C07C 51/412* (2013.01); *C12P 7/56* (2013.01); *B01D 11/0426* (2013.01)

(58) Field of Classification Search
CPC ......... C12P 7/56; C07C 51/412; C07C 51/48; C07C 57/13; C07C 69/68; B01D 11/04; B01D 11/0426
USPC .......................... 117/11, 68, 70, 74; 435/142
IPC .............. C30B 11/04,7/00; C07C 67/08; C12P 7/56, 7/44
See application file for complete search history.

(56) References Cited

U.S. PATENT DOCUMENTS

| | | | |
|---|---|---|---|
| 2,710,880 A | 6/1955 | Filachione et al. | |
| 3,786,096 A | 1/1974 | Konno | |
| 4,275,234 A | 6/1981 | Baniel et al. | |
| 4,698,303 A | 10/1987 | Bailey et al. | |
| 5,426,219 A | 6/1995 | Lehnhardt et al. | |
| 8,062,871 B2 | 11/2011 | Burgard et al. | |
| 9,422,217 B2 * | 8/2016 | Kon | C01F 5/10 |
| 2001/0014758 A1 | 8/2001 | Baniel et al. | |
| 2014/0349355 A1 * | 11/2014 | De Haan | C12P 7/44 |
| | | | 435/142 |
| 2015/0004663 A1 * | 1/2015 | De Haan | B01D 11/04 |
| | | | 435/136 |

FOREIGN PATENT DOCUMENTS

| | | |
|---|---|---|
| CN | 1241894 C | 2/2006 |
| CN | 101979368 A | 2/2011 |
| CN | 102690189 A | 9/2012 |
| GB | 173479 | 11/1922 |
| GB | 280969 | 6/1928 |
| JP | A-08-337552 | 12/1996 |
| JP | H09-500649 A | 1/1997 |
| WO | 94/19307 A1 | 9/1994 |
| WO | WO 95/03268 A1 | 2/1995 |
| WO | WO 00/17378 A2 | 3/2000 |

OTHER PUBLICATIONS

Jurriens et al, Analysis of Calcium Salts of Fatty Acid-Lactic Acid Condensates. American Association of Cereal Chemists Journal Oct. 21, 2009, pp. 669-675.*

Wilhelmi et al., 1948. A New Preparation of Crystalline Anterior Pituitary Growth Hormone. Journal of Biological chemistry, vol. 176, pp. 735-745.*

International Search Report issued in International Application No. PCT/EP2012/076696 dated Apr. 8, 2013.

Written Opinion of the International Searching Authority issued in International Application No. PCT/EP2012/076696 dated Apr. 8, 2013.

Mar. 1, 2016 Office Action Issued in U.S. Appl. No. 14/366,620.

(Continued)

*Primary Examiner* — Louise Humphrey
*Assistant Examiner* — Kailash C Srivastava
(74) *Attorney, Agent, or Firm* — Oliff PLC (57) ABSTRACT

A method for recovering lactic acid from an aqueous mixture including the steps of: providing an aqueous mixture including lactic acid and at least 5 wt. % dissolved magnesium chloride, based on the total weight of water and dissolved material in the aqueous mixture; extracting the lactic acid from the aqueous mixture into a first organic liquid including an organic solvent selected from the group consisting of C5+ ketones, diethylether and methyl-tertiary-butyl-ether, thereby obtaining an organic lactic acid solution and an aqueous waste liquid including magnesium chloride; and extracting the lactic acid from the organic lactic acid solution into an aqueous liquid, thereby obtaining an aqueous lactic acid solution and a second organic liquid. The method according to the invention allows a combined purification and concentration step for feed solutions of lactic acid.

22 Claims, 1 Drawing Sheet

(56) References Cited

OTHER PUBLICATIONS

Koopman et al.; "Efficient whole-cell biotransformation of 5-(hydroxymethyl)furfural into FDCA, 2,5-furandicarboxylic acid;" Bioresource Technology; 2010; pp. 6291-6296; vol. 101.
Aug. 18, 2015 Office Action Issued in Korean Patent Application No. 10-2014-7020313.
Wasewar et al., "Equilibrium Study for Reactive Extraction of Caproic Acid in Mibk and Xylene," Department of Chemical Engineering Visvesvaraya National Institute of Technology, vol. 3, pp. 829-835 (2001).
Goswami et al., "Fed-batch propionic acid production by Propionibacterium acidipropionici," Biomedical Engineering Journal, vol. 4, pp. 121-128 (2000).
Apr. 16, 2013 International Search Report issued in International Patent Application No. PCT/EP2012/076735.
Apr. 16, 2013 Written Opinion issued in International Patent Application No. PCT/EP2012/076735.
Mar. 27, 2013 Written Opinion issued in International Patent Application No. PCT/EP2012/076741.
Mar. 27, 2013 International Search Report issued in International Patent Application No. PCT/EP2012/076741.
Nov. 11, 2015 Office Action issued in Japanese Patent Application No. 2014-548085.
Nov. 11, 2015 Office Action issued in Japanese Patent Application No. 2014-548084.
Nov. 10, 2015 Office Action issued in Japanese Patent Application No. 2014-548079.
U.S. Appl. No. 14/366,620, filed Jun. 18, 2014 in the name of De Haan et al.
U.S. Appl. No. 14/366,628, filed Jun. 18, 21314 in the name of De Haan et al.
Oct. 15, 2015 Election of Species Requirement issued in U.S. Appl. No. 14/366,628.
Feb. 2, 2016 Office Action issued in U.S. Appl. No. 14/366,628.
Oct. 15, 2015 Election of Species Requirement issued in U.S. Appl. No. 14/366,620.
Jun. 1, 2016 Office Action issued in Vietnamese Patent Application No. 1-2014-02254.
Apr. 28, 2016 Office Action issued in Ukranian Patent Application No. a 2014 07598.
Substantial, Definition of Substantial by Merriam-Webster, May 21, 2016, 1 page, http://www.merriam-webster.com/dictionary/substantial.
Oct. 13, 2016 Office Action Issued in U.S. Appl. No. 14/366,628.
Doi et al. 1988. Nuclear Magnetic Resonance Studies on Unusual Bacterial Copolyesters of 3-Hyroxybutyrate and 4-Hydroxybutyrate. Macromolecules, vol. 21:2722-2727.
Oct. 18, 2016 Office Action Issued in U.S. Appl. No. 14/366,620.
Oct. 4, 2017 Office Action Issued in U.S. Appl. No. 14/366,620.
Dow Chemical Company 2002 MIBK Technical Data Sheet, (2002); accessed Sep. 30, 2017.
Britannica Academic (Lactic acid); http:/academic.eb.com/levels/collegiate/article/lactic-acid/46770; accessed Sep. 30, 2017.
Oct. 4, 2017 Office Action Issued in U.S. Appl. No. 14/366,628.
Jan. 11, 2018 Office Action issued in Indian Application No. 5067/CHENP/2014.
Apr. 1, 2016 Office Action issued in Korean Patent Application No. 10-2014-7020313.

* cited by examiner

LACTIC ACID EXTRACTION

This application is a U.S. national stage application of PCT/EP2012/076696 filed Dec. 21, 2012, and claims priority to U.S. Provisional Application No. 61/579,730 filed Dec. 23, 2011 and EP 11195691.8 filed Dec. 23, 2011.

The invention is directed to a method for preparing a lactic acid solution using extraction.

Isolating lactic acid from an aqueous mixture comprising impurities such as salts can be difficult. Lactic acid can be manufactured via fermentation of a carbon source, such as carbohydrates or glycerol, by micro-organisms. In such a fermentation process a carbohydrate source is typically fermented by means of a micro-organism to form lactic acid. The liquid wherein the carbohydrate source is fermented is called the fermentation broth or the fermentation medium.

The formation of lactic acid during fermentation will result in a decrease of the pH of the fermentation broth. Since such a decrease in pH can damage the micro-organism's metabolic process, it is common practice to add a neutralizing agent, i.e. a base, in the fermentation media in order to neutralize the pH. As a result, lactic acid produced in the fermentation media is typically present in the form of a lactate salt.

Although there are micro-organisms that are to some extent resistant to acidic environments, such that fermentation can be conducted at a low pH (e.g. at a pH of 3), even in these processes at least part of the lactic acid is obtained as a lactate salt.

To recover the lactic acid from the fermentation broth after fermentation, downstream processing is required. In such processing, the lactate salt in the fermentation broth needs to be converted into lactic acid. Also, the lactic acid (or lactate if not yet converted) needs to be isolated from the fermentation broth. Since a fermentation broth comprises many compounds, including significant amounts of biomass (such as micro-organisms) and salt (originating from the neutralizing agent), recovering and isolating lactic acid can be rather complex, typically requiring multiple processing steps and leading to waste material, in particular salt waste.

WO95/03268 describes a process for recovering an organic acid from a fermentation broth by clarifying the broth to remove at least a substantial portion of the impurities therein, producing a clarified feed; acidulating the clarified feed by adding a quantity of a mineral acid effective to lower the pH of the feed to between about 1.0 and about 4.5, producing an acidulated feed which is substantially saturated with respect to at least one electrolyte selected from the group consisting of MHSO4, M2SO4, M3PO4, M2HPO4, MH2PO4, and MNO3, where M is selected from the group consisting of Na, NH4, and K; extracting the acidulated feed with an extraction mixture which includes (a) water, (b) a mineral acid, in a quantity effective to maintain the pH of the feed between about 1.0 and about 4.5, and (c) an oxygenated solvent which has limited miscibility with water. The extraction produces a solvent extract and a first raffinate. The solvent extract is subjected to back-extraction with an aqueous liquid, thereby producing an organic acid-rich aqueous extract and an organic acid-depleted solvent raffinate.

WO00/17378 describes manufacture of lactic acid through fermentation, pH adjustment with Ca(OH)2 or Mg(OH), addition of HCl, and extraction with a solvent selected from amines, alcohols, and ethers, preferably iso-amyl alcohol, diisopropyl ether, and Alamine 336. The solvent containing the lactic acid is then contacted with water to generate a lactic acid solution, which is processed further.

CN101979368 describes extraction of acid from a solution containing a salt. The salt may be salt is sodium chloride. The extractant is methanol, ethanol, n-propanol, isopropanol, n-butanol, isobutanol, acetone, ethylene glycol, diethyl ether, methyl acetate or ethyl acetate.

JP8-337552 describes conversion of an acid salt to acid using sulphuric acid or HCl. The acid may, e.g., be lactic acid. Extraction takes place with an oxygenated saturated heterocycle type compound, e.g. tetrahydrofuran.

There are various problems associated with the processes described in the above-mentioned references. A particular problem with the sequence of extraction followed by back extraction is the formation of dilute liquids. Generally, when a compound is extracted from water using an organic liquid, and subsequently extracted from the organic liquid using water, the concentration of the compound in the product aqueous liquid is lower than that in the starting aqueous liquid. This is of course disadvantageous, because it generates dilute liquids which require further concentration.

There is therefore need in the art for an extraction/back extraction process for lactic acid, which allows the isolation of a lactic acid from a salt solution, without the formation of dilute acid solutions, and without the formation of salt crystals. The present invention provides such a process.

The present invention is directed to a method for recovering lactic acid from an aqueous mixture comprising the steps of
  providing an aqueous mixture comprising lactic acid and at least 5 wt. % dissolved magnesium chloride, based on the total weight of water and dissolved material in the aqueous mixture,
  extracting the lactic acid from the aqueous mixture into a first organic liquid comprising an organic solvent selected from the group consisting of C5+ ketones, diethylether and methyl-tertiary-butyl-ether, thereby obtaining an organic lactic acid solution and an aqueous waste liquid comprising magnesium chloride, and
  extracting the lactic acid from the organic lactic acid solution into an aqueous liquid, thereby obtaining an aqueous lactic acid solution and a second organic liquid.

It was found that the process according to the invention, which is characterised by the use of a specific acid, namely a lactic acid, in combination with a specific salt, namely a magnesium chloride, in a specific amount, namely in an amount of at least 5 wt. % dissolved magnesium chloride, in combination with a specific solvent leads to a process wherein the concentration of the lactic acid in the aqueous solution obtained after forward extraction and back extraction is higher than in the aqueous mixture before extraction. This concentration effect is for example advantageous when the aqueous lactic acid solution obtained after back extraction is to be concentrated, in which case energy costs are saved by having to evaporate less water to obtain a certain lactic acid concentration. Further advantages of the process according to the invention will become apparent from the further specification.

It is noted that U.S. Pat. No. 2,710,880 describes recovery of lactic acid from an aqueous solution using a water-miscible alcohol or ketone solvent, which preferably has 3-4 carbon atoms. The solution contains a salt, which preferably is a sulphate. The solvent is removed from the extract by distillation.

GB280969 describes extraction of lactic acid using an ether or a higher alcohol in the presence of a soluble sulphate, derived from sulphuric acid. Phosphoric acid and oxalic acid are mentioned as alternatives.

It is noted that CN101979368 describes extraction of acid from a solution containing a salt. The extractant is methanol, ethanol, n-propanol, isopropanol, n-butanol, isobutanol, acetone, ethylene glycol, diethyl ether, methyl acetate or ethyl acetate.

JP8-337552 describes conversion of an acid salt to acid, followed by extraction takes place with an oxygenated saturated heterocycle type solvent.

GB173479 describes reacting magnesium lactate with a suitable acid, followed by extraction. The acidification is carried out with sulphuric acid; the extraction is carried out with acetone or ether, adapted to dissolve the lactic acid. The solvent is removed by evaporation or distillation.

None of the references discussed above discloses a back extraction process. Therefore, these references are not relevant.

Not wishing to be bound by theory, it is believed that one or more of the following effects may occur in the extraction process according to the invention.

It may be that the presence of the magnesium chloride in the aqueous mixture enhances the extraction of the lactic acid from the aqueous mixture into the first organic liquid. This will contribute to the concentration effect described above.

Second, it may be that the dissolved magnesium chloride decreases the solubility of the organic solvent in water. In particular, at higher concentrations of dissolved magnesium chloride, less solvent (such as for example MIBK) might dissolve in the aqueous mixture. This effect may be stronger at higher temperatures, in particular in the temperature range of 20° to 100° C. Accordingly, forward and/or back extraction are preferably conducted at a temperature of at least 25° C., preferably at least 30° C., more preferably at least 40° C. It is contemplated that this effect holds true for ketones and ethers in general. The lower solubility of the organic liquid in water will result in streams with higher purity and less solvent losses in both the forward and back extraction and may thus lead to a more efficient process. In contrast, the solubility of water in alcohol and the solubility of alcohol in water increases when increasing the temperature in temperature range of 25° C. and 100° C.

Third, the solubility of the water in the organic solvent during extraction may also be decreased by the presence of the dissolved magnesium chloride.

Fourth, it was found that dissolved magnesium chloride may suppress emulsion formation, thereby enhancing phase-separation between the aqueous and organic liquids. This is in particular advantageous when the aqueous mixture comprises traces of biomass. Biomass originating from a fermentation process typically comprises compounds that can act as surfactants. Consequently, when an aqueous mixture comprising biomass is brought into contact with an organic solvent, typically an emulsion will be formed. Such emulsion formation is undesirable, because it may disrupt the extraction process and phase separation.

Further preferred embodiments of the present invention will be described below.

Figure 1:
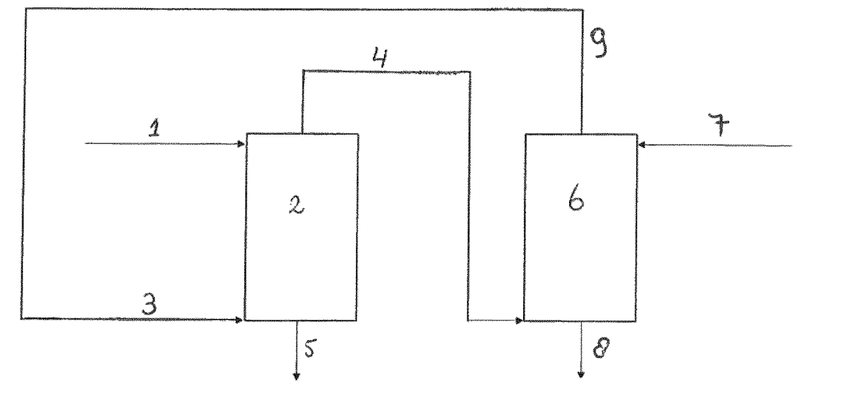

FIG. 1 gives a schematic representation of the an embodiment of the present invention. In FIG. 1, (1) is the aqueous starting mixture, which, where it is provided to an extraction reactor (2), where it is contacted with organic liquid (3). A stream (4), which comprises carboxylic acid in the organic liquid is withdrawn from the extraction reactor (2). Aqueous waste liquid (5) is also withdrawn from extraction reactor (2). Stream (4) comprising carboxylic acid in the organic liquid is provided to back-extraction reactor (6), where it is contacted with aqueous liquid provided through line (7). The product aqueous carboxylic acid solution is withdrawn through line (8). The organic liquid is withdrawn through line (9), and recycled to the extraction reactor (2) through line (3), optionally after intermediate purification steps (not shown).

The term "extraction" as used herein refers to liquid-liquid extraction, also known as solvent extraction. Solvent extraction is an extraction method based on the difference in solubility of a compound in two different liquids, i.e. in the present case the solubility of the lactic acid in water (present in the aqueous mixture and the aqueous liquid) relative to the solubility of the lactic acid in the organic solvent (present in the organic liquid). Forward extraction is the process wherein the compound to be extracted is extracted from the aqueous mixture into the organic liquid. Back extraction is the process wherein the compound to be extracted is extracted from the organic liquid into an aqueous liquid.

The term "solubility" as used herein refers to the maximum weight amount of a compound that can be dissolved in a certain amount of an aqueous mixture at a certain temperature.

Forward extraction and back extraction as used in the method of the invention are based on the difference in solubility of the lactic acid in water and the organic solvent at different temperatures. The solubility of a compound in one solvent relative to another solvent can be expressed in terms of the distribution ratio (DR). This ratio gives an indication how a compound will be distributed over the aqueous phase (e.g. the aqueous mixture) and the organic phase (e.g. the organic liquid) in a two-phase system at equilibrium. The distribution ratio may be defined as the ratio of the lactic acid concentration dissolved in the organic phase ([lactic acid]$_{organic}$) over the concentration of the lactic acid dissolved in water ([lactic acid]$_{water}$) provided that the two phases are in equilibrium with each other:

$$DR=[\text{lactic acid}]_{organic}/[\text{lactic acid}]_{water} \quad (1)$$

From formula (1) it can be concluded that the higher the distribution ratio, the more lactic acid will dissolve in the organic phase.

The distribution ratio depends on many variables, including the temperature and the specific composition of the organic and water phase. For example, the concentration of the dissolved magnesium chloride in the aqueous mixture and the type of solvent used will influence the distribution ratio. During forward extraction, the lactic acid should preferably dissolve better in the organic solvent than in water. Consequently, the distribution ratio in the forward extraction should be as high as possible. In particular, a high distribution ratio during forward extraction is desirable as any lactic acid still present in the waste liquid will directly lead to a decrease of the total lactic acid yield when this waste liquid cannot be reworked and/or recycled back to the process again, or used for other purposes and should be disposed off. In case the distribution ratio during forward extraction is high, relatively little lactic acid will be lost since most of the lactic acid will have been dissolved in the organic liquid.

It is preferred for the DR in forward extraction, also indicated as $D_{FE}$ to be at least 0.1, more in particular at least 0.4, still more in particular at least 0.8.

During back extraction, the opposite holds true. The lactic acid should preferably dissolve better in the aqueous phase than in the organic liquid. It is preferred for the DR in the backward extraction, also indicated as also indicated as $D_{BE}$ to be at most 0.5, more in particular at most 0.3, still more in particular at most 0.1.

If the distribution ratio for forward extraction is higher than the distribution ratio for back extraction, this will contribute to a concentration effect, wherein the aqueous lactic acid solution obtained after back extraction has a higher concentration of lactic acid than the aqueous mixture used as starting material in the forward extraction.

It is preferred for the ratio between $D_{FE}$ and $D_{BE}$ to be at least at least 1.1, more preferably at least 2. The ratio between $D_{FE}$ and $D_{BE}$ will generally not be more than 10. A range of 2 to 5 may be preferred.

The method of the invention comprises the step of providing an aqueous mixture comprising lactic acid and dissolved magnesium chloride. The aqueous mixture is the mixture to be extracted with the organic liquid.

The aqueous mixture is preferably an aqueous solution, since extraction can be more easily conducted when no solid matter is present. Such a solution may be referred to as an aqueous feed solution. Nevertheless, the presence of solid matter in the aqueous mixture is possible to a certain extent, dependent on the equipment used, as will be evident to the skilled person. Thus, the aqueous mixture can also be a suspension. Examples of solid matter that can be present in such a suspension are lactic acid in solid form, undissolved magnesium chloride and insoluble impurities.

The lactic acid content of in the aqueous mixture is preferably as high as possible. For example, the aqueous mixture may comprise at least 5 wt. %, preferably at least 10 wt. %, more preferably at least 15 wt. % lactic acid, based on the total weight of the aqueous mixture. Values of at least 20 wt. %, more in particular at least 25 wt. % may be particularly preferred. The water present in the aqueous mixture may be saturated with lactic acid.

In one embodiment, the aqueous mixture has a pH of 2 or lower, typically a pH below 1, for example a pH of 0-1. It is preferred for the pH to be relatively low, to ensure that the lactic acid is present in the mixture in acidic form, allowing extraction.

The aqueous mixture may further comprise impurities, in particular impurities originating from a fermentation process. Such impurities may be soluble or insoluble in the aqueous mixture. Examples of dissolved impurities are sugars, proteins, and salts. Insoluble biomass (e.g. microorganisms) and insoluble salts are examples of insoluble impurities. These impurities may all be typically present in a fermentation broth. More details on how to obtain the aqueous mixture are provided below.

The aqueous mixture comprises at least 5 wt. % dissolved magnesium chloride. The presence of dissolved magnesium chloride in the aqueous mixture has an advantageous effect in extraction, as described above. Dissolved magnesium chloride as used herein refers to magnesium chloride in its dissolved state, i.e. in the form of solvated ions, in water.

The aqueous mixture comprises at least 5 wt. % of dissolved magnesium chloride. To increase the effect of the invention, the salt concentration preferably is relatively high. It may be preferred for the salt concentration to be at least 10 wt. % more preferably at least 15 wt. %, even more preferably at least 20 wt. %, even more preferably at least 25 wt. % of dissolved magnesium chloride. Depending on the solubility of the salt, it may be possible to use at least 30 wt. %, even more preferably at least 35 wt. % dissolved magnesium chloride, based on the total weight the total weight of the aqueous mixture. (i.e. the total weight of the aqueous mixture excluding any solid matter). The maximum value is generally determined by the solubility of magnesium chloride, which is about 45 wt. %.

Preferably, the aqueous mixture is concentrated to a dissolved magnesium chloride concentration that is as high as possible, i.e. close to the solubility of the magnesium chloride, i.e. close to the maximum weight amount of the magnesium chloride that can be dissolved in the aqueous mixture, measured at the temperature at which forward extraction is conducted. Although undissolved magnesium chloride may be present in the aqueous mixture, this is not desirable. Therefore, the salt concentration in the aqueous mixture is preferably not higher than the solubility of the magnesium chloride in the aqueous mixture, so as to prevent precipitation. Accordingly, the aqueous mixture preferably has a dissolved magnesium chloride concentration within 10 wt. %, preferably within 5 wt. % of the solubility of the magnesium chloride in the aqueous mixture.

The dissolved magnesium chloride may originate from an acidulation reaction wherein a lactate salts is reacted with a hydrochloric acid. The dissolved magnesium chloride may also originate from adding magnesium chloride to an aqueous mixture to increase its dissolved magnesium chloride concentration. Combinations are of course also possible.

The aqueous mixture is preferably prepared by acidifying magnesium lactate with an hydrochloric acid, thereby forming an aqueous mixture comprising lactic acid and a magnesium chloride. The acidulation step is typically conducted by bringing the lactate salt in contact with an acidic solution. However, in some embodiments it may also be possible to contact the lactate salt with gaseous HCl.

The lactate salt may be in solid and/or dissolved from. In one embodiment, the lactate salt is provided in solid form. In this case, the acidulation step is conducted by bringing the lactate salt in contact with an acidic solution. The advantage of preparing the aqueous mixture from lactate salt in solid form is that very high lactic acid concentration can thus be obtained, such as concentration of at least 15 wt. %, in particular at least 25 wt. %, up to, e.g. 50 wt. %, or 40 wt. %.

The lactate salt may also be in dissolved form, typically as part of an aqueous solution. In this case, the acidulation step can be conducted by bringing the lactate salt in contact with an acidic solution or an acidic gas.

The acidulation step may also be conducted on a mixture of lactic acid and lactate salt. Such a mixture may for example be obtained in a low pH fermentation. The mixture may for example be an aqueous suspension.

The acid used in the acidulation step is typically a strong acid, such as hydrochloric acid or sulfuric acid. In view of the required presence of at least 5 wt. % of magnesium chloride, the use of hydrochloric acid is preferred. In such a case, an aqueous mixture is obtained comprising lactic acid and a chloride salt. HCl acidulation may for example be conducted by bringing the lactate salt in contact with an aqueous HCl solution or by bringing a lactate salt solution or suspension in contact with HCl gas.

When acidulation of the lactate salt is conducted by contacting it with an acidic solution, it preferably has an acid concentration as high as possible. Such a high acid concentration will result in an aqueous mixture with a high lactic acid concentration, which is desirable. The acidic solution therefore comprises at least 5 wt. %, more preferably at least 10 wt. % and even more preferably at least 20 wt. % acid, based on the total weight of the acidic solution. Acidulation is typically conducted using an excess of acid. The excess is preferably small, such that the aqueous mixture obtained is not highly acidic, which may not be desirable in view of further processing such a mixture. For example, the excess of acid used may be such that the resulting aqueous mixture has a pH 2 or lower, preferably a pH of 0-1.

In case an acidic gas is used (i.e. HCl gas), it may be contacted by bringing it in contact with a lactate solution or suspension. In particular, HCl gas may be blown through the solution or suspension. In case HCl gas is used, the HCl may originate from a thermal decomposition step, as described above.

Preferably, acidulation is conducted at a temperature of 75° C. or less. At higher temperatures, it becomes uneconomical to adapt equipment to the harsh conditions of an acidic environment at high temperatures.

After acidulation, solid material, if present, may be removed from the aqueous mixture, for example by filtration. As described above, the presence of solid material in the aqueous mixture in not desirable during extraction.

The aqueous mixture may be concentrated after acidulation prior to extraction to a concentration up to the solubility of the magnesium chloride, in particular to a desirable concentration of dissolved magnesium chloride. Specific values for this concentration are described above.

In one embodiment, magnesium lactate is used which originates from a fermentation process. Accordingly, the method of the invention may further comprise a fermentation step to form the lactic acid, which fermentation process comprises the steps of fermenting a carbon source, such as a carbohydrate, by means of a micro-organism in a fermentation broth to form lactic acid and neutralizing at least part of the lactic acid by addition of a base, in particular a magnesium base, thereby obtaining a magnesium lactate salt.

Fermentation processes for the manufacture of carboxylic acids are known in the art and require no further elucidation here. It is within the scope of the skilled person to select, using his common general knowledge, a suitable fermentation process, depending on the desired acid to be produced, the carbon source and the microorganism available.

The product of the fermentation process is a fermentation broth, which is an aqueous liquid comprising magnesium carboxylate, biomass, and optionally further components, such as impurities like are sugars, proteins, and salts.

If so desired, the fermentation broth may be subjected to a biomass removal step, e.g., a filtration step, before further processing. This is generally preferred for improving product quality.

Another intermediate step may be separation of solid reaction product, i.e. magnesium lactate, from the fermentation broth, before, after, or simultaneous with biomass removal, and optionally subjecting the magnesium lactate to a washing step. Depending on the concentration, magnesium lactate can precipitate in the fermentation medium. In one embodiment, the solid magnesium lactate is separated from the fermentation medium, e.g., by filtration, and subjected to an acidification step as described above.

Another intermediate step may be subjecting the fermentation broth to a concentration step to increase the concentration of magnesium lactate in the composition before acidification. This step may be carried out before, after, or simultaneous with biomass removal. Such a step may be attractive to increase the content of solid magnesium lactate, which may then be separated from the fermentation broth as described above, and processed as solid magnesium lactate in the process according to the invention.

Other intermediate steps, e.g., purification steps, may be carried out as desired, as will be evident to the skilled person.

In the method according to the invention, the aqueous mixture discussed above is subjected to an extraction step by contacting it with an organic liquid comprising an organic solvent selected from the group of C5+ ketones, diethylether, and methyl-tertiary-butylether, thereby obtaining an organic lactic acid solution and an aqueous waste liquid comprising magnesium chloride. In this forward extraction, the lactic acid is separated from the impurities present in the aqueous mixture by dissolving it in the first organic liquid. The impurities will remain in the aqueous mixture.

Preferably, the organic liquid comprises at least 90 wt. % of the organic solvent, preferably at least 95 wt. %, more preferably at least 99 wt. %. In one embodiment, the organic liquid is the organic solvent. Typically, small amounts of water can be present in the first organic liquid, in particular when the liquid (partly) comprises recycled organic solvent from a recycle step after extraction.

The organic solvent is selected from the group of C5+ ketones, diethylether, and methyl-tertiary-butylether. C5+ stands for ketones with at least 5 carbon atoms. It has been found that specific solvents compounds show good properties in the process according to the invention, where they show a good concentration effect. Selection of a suitable organic solvent may contribute to establishing a high distribution ratio during forward extraction. In that case, only a relatively small amount of lactic acid will be lost in the aqueous waste liquid.

As is illustrated in Example 10 of the present application, the solvents according to the invention show a concentration effect in the extraction of lactic acid. In contrast, other solvents, including isoamyl alcohol, diisopropyether, and trioctylamine (Alamine 336) mentioned as preferred in WO00/17378 do not show a concentration effect. The same goes for the mixture of 48% trioctylamine, 20% n-butanol, and 32% kerosene mentioned in Example 8 of WO00/17378.

In the present invention it is preferred to use ketones, in particular C5-C8 ketones. Mixtures may also be used. The use of C9+ ketones is less preferred, because these compounds are believed to show a lower concentration effect, and may result in more contaminants in the end product. The use of methyl-isobutyl-ketone (MIBK) has been found to be particularly attractive to obtain a good concentration effect.

Additionally, the use of ketones has been found to be preferred because they are stable under process conditions, in that they do not react or decompose to a substantial extent, thus giving rise to few contaminants, and allow a stable process operation.

As ethers, diethylether and methyl-tertiary-butylether may be used. It has been found, however, that they are less preferred, because the use of ethers results in more solvent loss and in more contaminants in the end product.

The method of the invention does not require the use of extracting agents, such as amines. In fact, the use of extracting agents in the organic solvent is generally undesirable. An extracting agent is a compound that forms a complex with the compound to be extracted (in this case lactic acid). However, the formation (during forward extraction) and breakage of the complex would require a relatively large amount of energy, such that the difference in temperature between forward and back extraction would need to be larger than necessary. Accordingly, the organic liquid preferably comprises no or substantially no extracting agents, in particular no or substantially no amine extracting agents.

Thus, the lactic acid in the method of the invention is preferably extracted in its neutral acidic form and not in the form of a salt or a complex.

The organic liquid is preferably essentially free of amines, ethers, and alcohols, which means that these compounds, if present at all, are each present in an amount of less than 2 wt. %, preferably less than 1 wt. %, more preferably less than 0.5 wt. %, calculated on the weight of the organic liquid.

The ratio of organic liquid to aqueous mixture used in forward extraction is determined by the following considerations. On the one hand, if the amount of organic liquid is relatively high, the efficiency of the extraction, expressed as the percentage of acid in the aqueous mixture which is extracted into the organic liquid will be high. On the other hand, a large amount of organic liquid will have to be used, and the concentration effect will be reduced. Conversely, if the amount of organic liquid is relatively low, the concentration effect will be improved, but the extraction efficiency will be reduced.

The Distribution Ratio (DR) defined above can give guidance in this respect. In one embodiment, the amount of organic liquid used in the forward extraction may be in the range of 0.5/DR to 1.5/DR times the amount of aqueous mixture.

The use of an amount of organic liquid in the range of 0.5/DR to 0.8/DR times the amount of aqueous mixture for forward extraction may be desirable for a good concentration effect. However, the yield of the extraction step may in this case be less than 99%. The use of an amount of organic liquid in the range of 1.3/DR to 1.5/DR times the amount of aqueous mixture for forward extraction may result in an extraction yield of over 99%, but typically has a less pronounced concentration effect. The use of an amount of organic liquid in the range of 0.8/DR to 1.3/DR, and in particular in the range of 1.0/DR to 1.2/DR, times the amount of aqueous mixture for forward extraction is most desirable, because both a good concentration effect and an extraction yield of over 99% can be obtained. The extraction yield as used herein refers to the weight percentage of the lactic acid that is extracted into the organic liquid during forward extraction.

Forward extraction is typically conducted by contacting the aqueous mixture with the first organic liquid, thereby obtaining an organic lactic acid solution and an aqueous waste liquid comprising the magnesium chloride. Preferably, the extraction is a counter-current extraction, i.e. the aqueous mixture and organic liquid are contacted with each other using counter-current streams. In such a configuration, a very efficient extraction of lactic acid into the organic liquid can be obtained, in particular with respect to the yield. The extraction is preferably conducted in an extraction column. In case the organic solvent used has a lower density than water (for example in case of MIBK), the organic solvent is preferably fed to the bottom of the column, while the aqueous mixture is fed at the top of the column. Consequently, two phases will form: an upper phase comprising the organic solvent and a lower phase comprising the aqueous mixture. At the interface of the two phases, any biomass and/or other solid matter present in the aqueous mixture will accumulate. As described above, the biomass does not cause emulsification due to the presence of the salt in the aqueous mixture. By feeding the organic solvent at the bottom of the column, the organic solvent will move upwards through the aqueous mixture, thereby extracting the lactic acid and forming an organic lactic acid solution. At the bottom of the column, an aqueous waste liquid can be obtained, typically in the form of an aqueous salt solution, which solution comprises the magnesium chloride.

Forward extraction may be conducted at a temperature of 20-100° C., preferably at a temperature of 30-80° C., for example at a temperature of 40-60° C. To reach the desirable temperature for forward extraction, the aqueous mixture and/or organic liquid may be heated prior to forward extraction. As described above, higher temperatures within the range of 20-100° C. are advantageous with respect to a decrease in solubility of the organic solvent in water. In addition, the distribution ratio may increase with increasing temperatures and/or may lead to a stronger concentration effect. In view of the possible corrosive conditions of the acidic aqueous mixture, a temperature above 60° C. may be disadvantageous. However, corrosion may for example be avoided by using plastic or glass-lined extraction equipment. The aqueous waste liquid formed in the forward extraction comprises the magnesium chloride. The aqueous waste liquid is typically obtained in the form of an aqueous salt solution, which solution comprises the magnesium chloride. This solution is relatively pure, since insoluble impurities typically remain at the interface of the water/organic interface during extraction.

To prevent acid loss from the system, it is preferred for the concentration of lactic acid in the waste liquid to be as low as possible. In one embodiment, the lactic acid concentration in the waste liquid is below 1 wt. %, in particular below 0.5 wt. %, more in particular below 0.1 wt. %. It has been found that extraction using the method according to the invention allows obtaining these very low acid losses.

To prevent solvent loss from the system, and to prevent problems in further processing, in particular when use is made of a thermal decomposition step, it is preferred for the concentration of solvent in the waste liquid to be as low as possible. In one embodiment, the solvent concentration in the waste liquid is below 1 wt. %, in particular below 0.5 wt. %, more in particular below 0.2 wt. %, and preferably below 0.1 wt. %. It has been found that extraction using the method according to the invention allows obtaining these very low solvent losses.

It is preferred for at least 80% of the acid present in the system to be in the organic phase after the forward-extraction, in particular at least 90%, preferably at least 95%, more preferably at least 93%, still more preferably at least 99%.

It is preferred for at least 90% of the magnesium chloride present in the system to be present in the aqueous waste liquid after the forward extraction, preferably at least 95%, more preferably at least 98%, in particular at least 99%.

The organic lactic acid solution is subsequently submitted to a back extraction step. Optionally, the organic lactic acid solution obtained in the forward extraction is subjected to an intermediate washing step to remove any impurities present in the organic lactic acid solution. Such impurities are typically entrained from the aqueous mixture, for example chloride or metal ions. In such a washing step, the organic lactic acid solution is contacted with a washing liquid. Such a step may decrease the amount of impurities, such as chloride and/or metal ions in the end product, i.e. the aqueous lactic acid solution. The removal of these ions may further prevent corrosion problems. The washing liquid is typically an aqueous liquid.

In one embodiment, part of the aqueous lactic acid solution formed as product in the back extraction is used as the washing liquid. In this embodiment, a small part, for example 0.5-5 wt. %, in particular 0.5-2 wt. %, of the product total aqueous lactic acid solution may be used for washing. The washing liquid may subsequently be recycled back to the aqueous mixture, where it will again be subjected to forward extraction. Care should be taken during washing not to remove too much acid from the organic liquid, as this will detrimentally affect the concentration of carboxylic acid in the final product. It is within the scope of the skilled person to determine suitable washing conditions.

The organic lactic acid solution formed in the forward extraction is, optionally after being washed, back extracted into an aqueous liquid, thereby obtaining an aqueous lactic acid solution and a second organic liquid. This step may be referred to herein as the second extraction or back extraction. The back extraction results in an aqueous lactic acid solution, which has a higher purity and in particular a lower salt concentration than the initial aqueous mixture. As explained above, the product aqueous lactic acid solution of the present invention typically has a higher concentration of lactic acid than the aqueous mixture.

The ratio of aqueous liquid to organic acid solution used in the back extraction is determined by the following considerations. On the one hand, if the amount of aqueous liquid is relatively high, the efficiency of the extraction, expressed as the percentage of acid in the organic acid solution which is extracted into the aqueous liquid will be high. On the other hand, a large amount of aqueous liquid will have to be used, and the concentration effect will be reduced. Conversely, if the amount of aqueous liquid is relatively low, the concentration effect will be improved, but the extraction efficiency will be reduced.

A suitable value for the ratio of aqueous liquid to organic acid solution used in that back extraction may be derived from the Distribution Ratio (DR) defined above. In one embodiment, the amount of aqueous liquid used in the back extraction is 0.5*DR to 1.5*DR times the amount of the organic lactic acid solution. These ratios may in particular be important with respect to the concentration effect of the present method. The use of an amount of aqueous liquid in the range of 0.5*DR to 0.8*DR times the amount of organic lactic acid solution for back extraction may be desirable for a good concentration effect. However, the yield of the back extraction step may in this case be less than 99% yield. The use of an amount of aqueous liquid in the range of 1.3*DR to 1.5*DR times the amount of organic lactic acid solution for back extraction may result in a back extraction yield of over 99%, but typically has a less pronounced concentration effect. The use of an amount of aqueous liquid in the range of 0.8*DR to 1.3*DR, and in particular in the range of 1.0*DR to 1.2*DR times the amount of organic lactic acid solution is most desirable, because both a good concentration effect and a back extraction yield of over 99% can be obtained. The back extraction yield as used herein refers to the weight percentage of the lactic acid that is extracted into the aqueous liquid during back extraction.

Back extraction is typically conducted by contacting the organic lactic acid solution with the aqueous liquid, thereby obtaining an aqueous lactic acid solution and a second organic liquid. The aqueous lactic acid solution is the product solution. If so desired, the second organic liquid, in its entirety or in part, may be recycled to the forward extraction as first organic liquid, optionally after having been subjected to a purification step. Preferably, the extraction is a counter-current extraction. In such a configuration, a very efficient extraction of lactic acid into the aqueous liquid can be obtained, in particular with respect to the yield.

The extraction is preferably conducted in an extraction column. In case the organic solvent used has a lower density than water, the aqueous liquid is preferably fed at the top of the column, while the organic lactic acid solution is fed at the bottom of the column. Consequently, two phases will form: an upper phase comprising the organic solvent and a lower phase comprising the aqueous liquid. By feeding the aqueous liquid at the top of the column, it will pass downward through the organic lactic acid solution, thereby extracting the lactic acid and forming an aqueous lactic acid solution. An aqueous lactic acid solution can then be recovered at the bottom of the column.

It is noted that it was contemplated to evaporate the organic solvent from the organic lactic acid solution after forward extraction, thereby directly obtaining the lactic acid. However, better results were obtained when using a back extraction in accordance with the present invention. Back extraction resulted in less impurities and a more energy efficient process.

Back extraction may be conducted at a temperature of 20-100° C., preferably at a temperature of 80° C. or lower, more preferably at a temperature of 60° C. or lower. Back extraction is preferably conducted at a temperature above 0° C., preferably a temperature of at least 10° C. due to energy costs associated with cooling. Temperatures equal or close to the temperature in the forward extraction are particular preferred for back extraction. This may save energy, because less heating and/or cooling is required between the different streams in the extraction process. Accordingly, in one embodiment the back extraction is conducted at a temperature that is within 10° C., for example within 5° C. of the temperature at which forward extraction is conducted. The use of a similar temperature in forward and back extraction is herein also referred to as isothermal conditions. Forward extraction and back extraction may be conducted at about the same temperature, for example using a temperature difference between forward and back extraction of less than 5° C.

In one embodiment, the extraction into the organic liquid (forward extraction) is conducted at a lower temperature than the extraction into the aqueous liquid (back extraction). Such an extraction method is also known as a regular temperature swing extraction. The temperature during back extraction is in this case 5-45° C., for example 10-20° C. higher than the temperature in forward extraction.

In another embodiment, the extraction into the organic liquid (forward extraction) is conducted at a higher temperature than the extraction into the aqueous liquid (back extraction). Such an extraction method may be indicated as a reverse temperature swing extraction. In the reverse temperature swing extraction, the back extraction step may in this case be conducted at a temperature that is 10-50° C. or 20-30° C. lower than the temperature at which forward extraction is conducted. It has been found that operating extraction in reverse temperature swing mode may lead to an increased concentration of acid in the product.

In one embodiment in the process according to the invention the organic lactic acid solution is brought into thermal contact with the second organic liquid using a heat exchanger. This is advantageous when forward and back extraction are conducted at different temperatures.

The aqueous lactic acid solution obtained after back extraction as performed according to the present invention has a higher lactic acid concentration than the aqueous mixture which was fed to the forward extraction. This is also illustrated in the examples below.

The extent of the concentration effect of the method of the invention depends, among others, on the ratio of the organic liquid and aqueous mixture used in forward extraction, the ratio of the aqueous liquid and organic lactic acid solution used for back extraction, the temperature at which the extraction steps are conducted, the type of organic liquid used and the amount of dissolved magnesium chloride present in the aqueous mixture. Furthermore, it is preferred to select the process conditions in such a manner that so as to obtain a high extraction yield. In this respect, it is preferred that the weight amount of organic liquid used in forward extraction is 1.0/DR to 1.2/DR times the weight amount of aqueous mixture while the weight amount of aqueous liquid used in back extraction is 1.0*DR to 1.2*DR times the weight amount of organic lactic acid solution. It is even more preferred that the weight amount of organic liquid used in forward extraction is 1.1/DR to 1.2/DR times the weight amount of aqueous mixture while the weight amount of aqueous liquid used in back extraction is 1.1*DR to 1.2*DR times the weight amount of organic lactic acid solution. These weight ratios result in a particular good concentration effect when additionally combined with a forward extraction temperature of 50-60° C. and a dissolved magnesium chloride concentration of at least 10 wt. %, based on the total amount of water and dissolved material present in the aqueous mixture. The organic liquid used is in this case preferably a ketone, more preferably MIBK. The back-extraction is in this case preferably conducted at 20-60° C., more preferably at 50-60° C. An even better concentration effect is obtained when using a magnesium chloride concentration of at least 15 wt. % instead of at least 10 wt. %, based on the total amount of water and dissolved material present in the aqueous mixture. Thus, the following combination of parameters may result in particular good concentration effect and may at the same time result in a good extraction yield:
  a magnesium chloride concentration of at least 10 wt. %, based on the total amount of water and dissolved material present in the aqueous mixture;
  a forward extraction temperature of 30-60° C., in particular 50-60° C.;
  a back extraction temperature of 20-60° C.;
  a weight amount of organic liquid used in forward extraction that is 1.1/DR to 1.2/DR times the weight amount of aqueous mixture;
  a weight amount of aqueous liquid used in back extraction that is 1.1*DR to 1.2*DR times the weight amount of organic lactic acid solution;
  the organic liquid being a C5+ ketone, preferably a C5-C8 ketone, more preferably MIBK.

The above combination works even better when using a magnesium chloride concentration of at least 15 wt. %, based on the total amount of water and dissolved material present in the aqueous mixture.

The total yield of the method of the invention depends both on the extraction yield in forward extraction and the extraction yield in back extraction.

The yield of forward extraction can be increased by conducting the forward extraction with counter-current streams (see also above). Such counter-current extraction can be conducted in one or more vessels (e.g. a mixer or settler). The yield of the extraction step can be increased by increasing the size and/or the number of the vessel(s). When using more than one vessel, the vessels are connected in series with each other. In this case, the second or further vessel further extracts the aqueous liquid obtained after extraction in the previous vessel. Preferably however, forward extraction is conducted in one vessel (e.g. an extraction column) that is sufficiently large to obtain the desired high yield (typically above 99%). For example, large extraction columns with a height of 10-20 meter are known in the art. The skilled person will be able to adjust the size and/or number of the vessels to obtain a yield of 99% or more.

The yield of back extraction can be increased in the same way as described above for forward extraction. In case more than one vessel is used, the second or further vessel further extracts the organic liquid obtained after extraction in the previous vessel.

The method of the invention may further comprise the step of concentrating the product aqueous lactic acid solution by evaporation of water. The water evaporated in this step may be recycled by reusing it as the aqueous liquid in back extraction. It is possible for the product aqueous lactic acid solution to comprise a minor amount of organic solvent and residue from the extraction step, if present e.g. of the order of 0.1-3 wt. % based on the total amount of the aqueous lactic acid solution. Where an evaporation step is carried out, organic solvent is also typically evaporated in the concentration step, often enhanced by a stripping effect of water.

As indicated above, the second organic liquid obtained in the back extraction can be recycled by reusing it as the first organic liquid in the forward extraction.

In one embodiment, the method of the invention comprises the step of subjecting the aqueous waste liquid comprising magnesium chloride obtained in forward extraction to a thermal decomposition step at temperatures of at least 300° C., thereby forming a magnesium oxide and HCl. In this step, the chloride salt is thermally hydrolyzed under formation of magnesium oxide and HCl, which compounds can be recycled in other stages in a process for lactic acid preparation. For example, the magnesium oxide may be used in a fermentation process, for example as a neutralizing agent or as a precursor thereof. The magnesium oxide may for this purpose be brought in contact with water to obtain a magnesium hydroxide slurry. Furthermore, HCl may be used to acidify magnesium lactate obtained in a fermentation process. HCl is typically dissolved in water during or after thermal decomposition, thereby obtaining a HCl solution. Thus, the thermal decomposition step provides for a process wherein the waste material is recycled and wherein consequently relatively little waste is produced.

The method of the invention is preferably a continuous process. However, it may also be conducted as a batch process.

The invention will further be illustrated by the following examples, without being limited thereto or thereby.

Example 1: Lactic Acid Extraction in Absence of Dissolved Salt—Comparative

A lactic acid feed solution was prepared by adding 304 g of crystalline lactic acid to 745 g water and mixing to complete dissolution. The thus prepared feed solution comprised 29 wt % of lactic acid.

In the forward extraction an amount of 101 g MIBK was added to 1000 g of the lactic acid feed solution (weight-based ratio of 1:10). The resulting two phase system was stirred at 20° C. for 30 minutes with sufficient speed to ensure that both phases were well dispersed. Hereafter, the stirring was stopped, the phases were allowed to separate and the lactic acid loaded MIBK layer was separated from the depleted aqueous lactic acid solution.

In the back extraction 5.2 g of water was added to 53 g of this lactic acid loaded MIBK layer (weight-based ratio of 1:10). The resulting two phase system was stirred at 20° C. for 30 minutes with sufficient speed to ensure that both phases were well dispersed. Hereafter, the stirring was stopped, the phases were allowed to separate and a sample was taken from the aqueous bottom phase. The concentration of lactic acid in this sample was 19.4 wt % (determined via potentiometric titration).

This example shows that extraction conducted in the absence of dissolved magnesium chloride as used in the method according to the present invention reduces the lactic acid concentration from 29 wt % in the feed solution to 19.4 wt % in the product aqueous solution.

Example 2: Lactic Acid Extraction in the Presence of Dissolved Salt

A lactic acid feed solution (aqueous mixture) was prepared by adding magnesium chloride hexahydrate (790 g) to a solution of 700 g of crystalline lactic acid in 924 g water and mixing to complete dissolution. The thus prepared feed solution comprised 29 wt % of lactic acid and 15.3 wt % of magnesium chloride.

In the forward extraction an amount of 100 g MIBK was added to 1000 g of the lactic acid feed solution (weight-based ratio of 1:10). The resulting two phase system was stirred at 20° C. for 30 minutes with sufficient speed to ensure that both phases were well dispersed. Hereafter, the stirring was stopped, the phases were allowed to separate and the lactic acid loaded MIBK layer was separated from the depleted aqueous lactic acid solution. In the back extraction 4.7 g of water was added to 46.9 g of this lactic acid loaded MIBK layer (weight-based ratio of 1:10). The resulting two phase system was stirred at 20° C. for 30 minutes with sufficient speed to ensure that both phases are well dispersed.

Hereafter, the stirring is stopped, the phases were allowed to separate and a sample was taken from the aqueous bottom phase. The concentration of lactic acid in this sample was 34.8 wt % (determined via potentiometric titration).

This example shows that the presence of dissolved magnesium chloride salt in the forward extraction increases the lactic acid concentration from 29 wt % in the feed solution to 34.8 wt % in the aqueous solution after back extraction.

In case the solution would be subjected to an evaporation step after extraction, the increased lactic acid concentration in the aqueous solution from the back extraction would thus reduce the amount of water that needs to be evaporated from the lactic acid product compared to the aqueous solution obtained after back extraction from the feed solution without dissolved magnesium chloride in example 1 by a factor 2.

Example 3: Regular Temperature Swing Lactic Acid Extraction

In the forward extraction an amount of 100 g MIBK was added to 1000 g of the lactic acid feed solution (weight-based ratio of 1:10) as prepared in example 2 above. The resulting two phase system was stirred at 20° C. for 30 minutes with sufficient speed to ensure that both phases were well dispersed. Hereafter, the stirring was stopped, the phases were allowed to separate and the lactic acid loaded MIBK layer was separated from the depleted aqueous lactic acid solution. In the back extraction 6.9 g of water was added to 67.2 g of this lactic acid loaded MIBK layer (weight-based ratio of 1:10). The resulting two phase system was stirred at 60° C. for 30 minutes with sufficient speed to ensure that both phases are well dispersed. Hereafter, the stirring is stopped, the phases were allowed to separate and a sample was taken from the aqueous bottom phase. The concentration of lactic acid in this sample was 36.2 wt % (determined via potentiometric titration).

This example shows that applying a combination of dissolved magnesium chloride and a higher temperature in the back extraction yields an increased lactic acid concentration of 36.2 wt % in the aqueous solution after back extraction compared to the isothermal conditions applied in example 2.

It can be concluded that applying an increased temperature in the back extraction is an efficient means of further concentrating the lactic acid during extraction.

Example 4: Reverse Temperature Swing Lactic Acid Extraction

In the forward extraction an amount of 100 g MIBK was added to 997 g of the lactic acid feed solution (weight-based ratio of 1:10) as prepared in example 2. The resulting two phase system was stirred at 60° C. for 30 minutes with sufficient speed to ensure that both phases were well dispersed. Hereafter, the stirring was stopped, the phases were allowed to separate and the lactic acid loaded MIBK layer was separated from the depleted aqueous lactic acid solution. In the back extraction 5.8 g of water was added to 58 g of this lactic acid loaded MIBK layer (weight-based ratio of 1:10). The resulting two phase system was stirred at 20° C. for 30 minutes with sufficient speed to ensure that both phases were well dispersed. Hereafter, the stirring was stopped, the phases were allowed to separate and a sample was taken from the aqueous bottom phase. The concentration of lactic acid in this sample was 37.1 wt % (determined via potentiometric titration).

This example shows that applying a combination of dissolved magnesium chloride and a higher temperature in the forward extraction yields an increased lactic acid concentration of 37.1 wt % in the aqueous solution after back extraction compared to the isothermal conditions applied in example 2.

It can be concluded that applying an increased temperature in the forward extraction is an efficient means of further concentrating the lactic acid during extraction.

Example 5: Increased Temperature Lactic Acid Extraction

In the forward extraction an amount of 100 g MIBK was added to 996 g of the lactic acid feed solution (weight-based ratio of 1:10) as prepared in example 2. The resulting two phase system was stirred at 60° C. for 30 minutes with sufficient speed to ensure that both phases were well dispersed. Hereafter, the stirring was stopped, the phases were allowed to separate and the lactic acid loaded MIBK layer was separated from the depleted aqueous lactic acid solution. In the back extraction 6.2 g of water was added to 63 g of this lactic acid loaded MIBK layer (weight-based ratio of 1:10). The resulting two phase system was stirred at 60° C. for 30 minutes with sufficient speed to ensure that both phases were well dispersed. Hereafter, the stirring was stopped, the phases were allowed to separate and a sample was taken from the aqueous bottom phase. The concentration of lactic acid in this sample was 36.0 wt % (determined via potentiometric titration).

This example shows that applying a combination of dissolved magnesium chloride and a higher temperature in the forward as well as back extraction yields an increased lactic acid concentration of 36.0 wt % in the aqueous solution after back extraction compared to the isothermal conditions applied in example 2. It can be concluded that isothermal operation at an increased temperature during forward and extraction is an efficient means of further concentrating the lactic acid during extraction.

Example 6: Comparison of MIBK and Isoamyl Alcohol

This experiment was conducted to compare the stability of two solvents, MIBK and Isoamyl alcohol in contact with the lactic acid feed solution as prepared in example 1. For each solvent a closed glass reactor was filled with 20 g of solvent and 20 g of the lactic acid feed solution, put in an oven to maintain a temperature of 60° C. and shaken continuously.

After 3 hrs, 24 hrs (1 day) and 168 hrs (1 week) the shaking was stopped for 1 hour to allow the phases to settle, a sample was taken from the solvent top layer, and the composition of the solvent top layer analyzed by gas chromatography. The results show that even after 168 hrs no changes in the purity of the MIBK could be detected while in case of isoamyl alcohol 14.6 area % of isoamyllactate was formed after 3 hrs. In the 24 hrs and 168 hrs samples the isoamyllactate concentration was found to have increased further to 22.5 area %.

This example shows that esters with the lactic acid are formed when alcohols such as isoamyl alcohol are used as organic extraction solvent while ketones such as MIBK are stable organic solvents. It can be concluded that unstable organic solvents such as alcohols are unsuitable as extraction solvent and that stable organic solvents such as ketones are suitable extraction solvents.

Example 7: Effect of Dissolved Salt Concentration and Temperature on Distribution Ratio 100 g MIBK organic solvent was added to 100 g of an aqueous solution with the desired MgCl2 and initial lactic acid concentration of 20 wt %. The resulting two phase system was stirred at 20° C. or 60° C. for 30 minutes with sufficient speed to ensure that both phases are well dispersed. Hereafter, the stirring is stopped, the phases were allowed to separate and samples were taken from both phases. The concentration of lactic acid (wt %) in these samples was determined by potentiometric titration. Hereafter the distribution ratio was calculated as the ratio of the lactic acid concentration (wt %) in the MIBK organic solvent phase divided by the lactic acid concentration (wt %) in the aqueous phase. The results are shown in Table 1.

TABLE 1

|  | Lactic acid distribution ratio (wt %/wt %) | |
| --- | --- | --- |
| $MgCl_2$ (wt %) | 20° C. | 60° C. |
| 0 | 0.16 | 0.19 |
| 10.5 | 0.33 | 0.37 |
| 16.0 | 0.49 | 0.56 |

This example shows that with increasing salt concentration the lactic acid distribution ratio increases significantly. Furthermore, the example also shows that the distribution ratio can be increased by raising the temperature. It can be concluded that the presence of salt and/or an increase in temperature significantly increase the extraction efficiency of carboxylic acids from the aqueous feed stream into the organic solvent.

Example 8: Effects of Dissolved Salt Concentration and Temperature on Solvent Solubility 50 g MIBK organic solvent was added to 100 g of an aqueous solution with a specified MgCl2 concentration and the resulting two phase system stirred at a specified temperature for 30 minutes with sufficient speed to ensure that both phases are well dispersed. Hereafter, the stirring is stopped, the phases were allowed to separate and a sample was taken from the aqueous bottom phase. The concentration of MIBK in this sample was determined by gas chromatography. The experiment was conducted for three different MgCl2 concentrations (0, 15 and 30 wt. %) at two different temperatures (20° C. and 60° C.). The results are shown in Table 2.

TABLE 2

|  | MIBK solubility (wt %) | |
| --- | --- | --- |
| $MgCl_2$ (wt %) | 20° C. | 60° C. |
| 0 | 1.8 | 1.4 |
| 15 | 0.48 | 0.20 |
| 30 | 0.17 | 0.11 |

This example shows that the addition of salt significantly reduces the solubility of the MIBK organic solvent in the aqueous phase. It can be concluded that the presence of salt significantly reduces the loss of organic solvent in the aqueous phase after extraction of the carboxylic acid.

Example 9: Pilot Action Lactic Acid

The pilot extraction experiments were conducted in a Pulsed Disc and Donut Column (PDDC) pilot set-up containing an active column section of four thermo stated glass segments of each 1.04 m length and 40 mm internal diameter. This active section was enclosed on both sides by 42 cm long settlers, both having an inner diameter of 80 mm. The column internals consisted of alternately placed disc and doughnut baffles with a spacing of 8.4 mm made of PVDF to ensure wetting by the organic solvent phase. The bottom settler is connected to a piston type pulsator to pulse the liquid in the column at a desired frequency and amplitude. The aqueous solutions were introduced in the top and the MIBK organic solvent at the bottom of the column. The column was operated with the MIBK organic solvent as the continuous phase and the aqueous solutions as the dispersed phase. The interface level in the bottom settler was observed visually and controlled via a manually operated valve in the aqueous stream leaving the bottom of the column. The MIBK organic solvent was allowed to leave the column top settler via an overflow.

In the forward extraction the lactic acid feed solution (7 kg/hr), prepared in a similar way as in Example 2, was contacted counter currently in the PDDC pilot setup with MIBK (9.3 kg/hr) at a temperature of 60° C. The pulsator was operated with a frequency of 90 min-1 and amplitude of 11 mm. The lactic acid loaded MIBK organic solvent was collected during several hrs to collect a sufficient amount for the back extraction. In the back extraction the lactic acid loaded MIBK organic solvent (10.4 kg/hr) was counter currently contacted with water (2.5 kg/hr) in the PDDC setup at a temperature of 20° C. The pulsator was operated with a frequency of 67.5 min-1 and amplitude of 11 mm. Samples were taken from the aqueous bottom phase. The concentration of lactic acid in this sample was 34.5 wt % (determined via potentiometric titration).

This example shows that applying a dissolved magnesium chloride combined with a higher temperature in the forward extraction increases the lactic acid concentration from 29 wt % in the feed solution to 34.5 wt % in the aqueous solution after back extraction. It can be concluded that applying a dissolved magnesium chloride eventually combined with an increased temperature in the forward extraction in an extraction column is an efficient means of concentrating the lactic acid during extraction.

Example 10: Comparison of Different Solvents in Lactic Acid Extraction

Feed solutions were prepared comprising 29 wt % lactic acid and 15 wt % magnesium chloride. The solutions were stirred overnight. Extraction took place as follows: 1000 g of a feed solution was mixed with approximately 100 g of solvent and stirred at 20° C. for minimum of 15 minutes. The mixture was transferred to a separation funnel where phases were separated. Samples of both phases were taken for analysis. Then approximately 100 g of organic phase was mixed with 10 g of pure water and stirred for minimum of 15 min at 20° C. Subsequently the whole mixture was again transferred to the separation funnel, phases were left to separate and samples of both phases are taken. Samples were analysed on acid content. The results are presented in Table 3, where inv stands for Example according to the invention and comp stands for comparative example.

TABLE 3

| | Solvent | [lactic acid] feed (wt. %) | [lactic acid] product (wt. %) |
|---|---|---|---|
| 1 inv | 2-pentanone | 29 | 30 |
| 2 inv | methylisobutyl ketone | 29 | 35 |
| 3 inv | cyclo-hexanone | 29 | 32 |
| 4 inv | 2-hexanone | 29 | 35 |
| 5 inv | acetophenone | 29 | 34 |
| 6 inv | 2-heptanone | 29 | 34 |
| 7 inv | 2-octanone | 29 | 30 |
| 8 inv | diethylether | 29 | 38 |
| 9 inv | methyl-tertiary-butyl-ether | 29 | 37 |
| 10 comp | ethyl propyl ether | 29 | 25 |
| 11 comp | diisopropyl ether | 29 | 21 |
| 12 comp | methyl ethyl ketone | 29 | —* |
| 13 comp | trioctylamine (TOA) | 29 | 13 |
| 14 comp | n,n-diethyl-m-toluamide | 29 | 27 |
| 15 comp | toluene | 29 | 1 |
| 16 comp | isoamyl alcohol | 29 | 23 |
| 17 comp | TOA-BuOH-Kerosene** | 29 | 11 |

*no phase separation took place in forward extraction. No results were obtained
**48 wt % trioctylamine, 20 wt % n-butanol and 32 wt % kerosene The data in Table 3 show that for the C5+ ketones concentration occurred, with best results being obtained for methyl isobutyl ketone.

Of the ethers, only diethylether and methyl-tertiary-butyl-ether showed a concentration effect. It has to be noted however, that while these compounds indeed showed good extraction properties, it has associated disadvantages, residing int al. in more solvent loss and more contaminants in the product.

Example 11: Comparison of Different Salts in Lactic Acid Extractions

Feed solutions were prepared comprising 29 wt % lactic acid and a specified amount of a specific salt. The solutions were stirred overnight. Extraction experiments were carried out in accordance with the procedure described in Example 10, using methyl isobutylketone as solvent. The results are presented in Table 4, where inv stands for Example according to the invention and comp stands for comparative example.

TABLE 4

| | salt (concentration) | [lactic acid] feed (wt. %) | [lactic acid] product (wt. %) |
|---|---|---|---|
| 1 inv | MgCl2 (15 wt. %) | 29 | 35 |
| 2 comp | CaCl2 (18 wt. %) | 29 | 18 |
| 3 comp | NaCl (19 wt. %) | 29 | 23 |
| 4 comp | KCl (24 wt. %) | 29 | 21 |
| 5 comp | NaNO3 (27 wt. %) | 29 | 24 |
| 6 comp | Na2SO4 (23 wt. %) | 29 | 23 |
| 7 comp | Na3PO4 (18 wt. %) | 29 | 6.4 |
| 8 comp | (NH4)2SO4 (23 wt. %) | 29 | 26 |

As can be seen from Table 4, only MgCl2 gives a concentration effect. All other salts give a dilution effect. This is particularly remarkable because for all salts the concentration is higher than is used for MgCl2, and a higher concentration is believed to promote a concentration effect.

The invention claimed is:

1. Method for recovering lactic acid from an aqueous mixture comprising the steps of
   providing an aqueous mixture comprising lactic acid and at least 5 wt. % dissolved magnesium chloride, based on the total weight of water and dissolved material in the aqueous mixture,
   a first extraction comprising extracting the lactic acid from the aqueous mixture into a first organic liquid comprising at least 90 wt. % of an organic solvent selected from the group consisting of C5+ ketones, diethylether and methyl-tertiary-butyl-ether, thereby obtaining an organic lactic acid solution and an aqueous waste liquid comprising magnesium chloride, and
   a second extraction comprising extracting the lactic acid from the organic lactic acid solution into an aqueous liquid, thereby obtaining an aqueous lactic acid solution and a second organic liquid.

2. Method according to claim 1, wherein the aqueous mixture comprises at least 15 wt. % dissolved magnesium chloride, based on the total weight of water and dissolved material in the aqueous mixture.

3. Method according to claim 1, wherein the organic solvent is a C5+ ketone.

4. Method according to claim 3, wherein the solvent is a C5-C8 ketone.

5. Method according to claim 1, wherein the first extraction is conducted at a temperature of at least 30° C.

6. Method according to claim 1, wherein the second extraction is conducted at a lower temperature than a temperature at which the first extraction is conducted.

7. Method according to claim 6, wherein the second extraction is conducted at a temperature 10° C. to 50° C. lower than the temperature at which the first extraction is conducted.

8. Method according to claim 1, wherein the second extraction is conducted within 10° C. of a temperature at which the first extraction is conducted.

9. Method according to claim 1, wherein the first organic liquid comprises substantially no extractants.

10. Method according to claim 1, wherein the first organic liquid is essentially free of amines, ethers, and alcohols, which means that these compounds, if present at all, are each present in an amount of less than 2 wt. %, calculated on the weight of the organic liquid.

11. Method according to claim 1, wherein the aqueous mixture has a pH of 2 or lower.

12. Method according to claim 1, which further comprises
subjecting the aqueous waste liquid comprising magnesium chloride to a thermal decomposition step at a temperature of at least 300° C., thereby decomposing the magnesium chloride salt to a magnesium oxide and HCl; and
dissolving the HCl formed in the thermal decomposition step in water, thereby obtaining a HCl solution; and
optionally recycling the magnesium oxide in a fermentation process as a neutralizing agent or precursor thereof.

13. Method according to claim 1, further comprising a fermentation step to form the lactic acid, which fermentation process comprises the steps of fermenting a carbon source by means of a micro-organism in a fermentation broth to form lactic acid and neutralizing at least part of the lactic acid by adding a magnesium base, thereby obtaining the corresponding lactate.

14. Method according to claim 1, wherein the method further comprises the step of
preparing an aqueous mixture by acidifying a lactate salt with an acid, thereby obtaining an aqueous mixture.

15. Method according to claim 14, wherein the lactate salt is acidified with HCl and further comprising the step of concentrating the thus obtained aqueous mixture prior to extraction to a dissolved salt concentration of at least 5 wt. %, based on the total weight of water and dissolved material in the aqueous mixture.

16. Method according to claim 1, wherein the aqueous mixture comprises at least 20 wt. % dissolved magnesium chloride based on the total weight of water and dissolved material in the aqueous mixture.

17. Method according to claim 1, wherein the method further comprises a step of preparing the aqueous mixture by acidifying a mixture of lactic acid and magnesium lactate salt with HCl.

18. Method according to claim 1, further comprising subjecting the magnesium chloride solution to a thermal decomposition step at a temperature of at least 300° C., thereby decomposing the $MgCl_2$ to magnesium oxide (MgO) and HCl.

19. Method according to claim 18, wherein the MgO is recycled for use in a fermentation process as a neutralizing agent.

20. Method according to claim 19, further comprising bringing the MgO into contact with water, thereby obtaining $Mg(OH)_2$, which is recycled for use in a fermentation process as a neutralizing agent.

21. Method according to claim 18, wherein said HCl obtained in the thermal decomposition step is used in an acidifying step either as HCl gas or as an aqueous HCl solution, said solution being obtained through dissolving the HCl formed in the thermal decomposition step in water.

22. Method for recovering lactic acid from an aqueous mixture comprising the steps of
providing an aqueous mixture comprising lactic acid and at least 5 wt. % dissolved magnesium chloride, based on the total weight of water and dissolved material in the aqueous mixture,
a first extraction comprising extracting the lactic acid from the aqueous mixture into a first organic liquid comprising at least 90 wt. % of an organic solvent selected from the group consisting of C5+ ketones, diethylether and methyl-tertiary-butyl-ether, thereby obtaining an organic lactic acid solution and an aqueous waste liquid comprising magnesium chloride, wherein the first extraction is conducted at a temperature of at least 30° C., and
a second extraction comprising extracting the lactic acid from the organic lactic acid solution into an aqueous liquid, thereby obtaining an aqueous lactic acid solution and a second organic liquid, wherein the second extraction is conducted at a temperature 10° C. to 50° C. lower than the temperature at which the first extraction is conducted.

* * * * *